(12) United States Patent
Strong et al.

(10) Patent No.: US 9,642,983 B2
(45) Date of Patent: *May 9, 2017

(54) CATHETER HAVING A MULTI-SECTION TUBULAR MEMBER AND METHOD OF MAKING THE SAME

(71) Applicant: BOSTON SCIENTIFIC SCIMED, INC., Maple Grove, MN (US)

(72) Inventors: Jeffery John Strong, Coon Rapids, MN (US); Kristi Flury, Maple Grove, MN (US); Chrismar L. Scribner, Bloomington, MN (US); Melissa Sjoquist, Hopkins, MN (US); Craig C. Belton, Shakopee, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 239 days.

This patent is subject to a terminal disclaimer.

(21) Appl. No.: 14/523,860

(22) Filed: Oct. 25, 2014

(65) Prior Publication Data
US 2015/0196733 A1    Jul. 16, 2015

Related U.S. Application Data

(63) Continuation of application No. 12/724,264, filed on Mar. 15, 2010, now Pat. No. 8,870,906, which is a
(Continued)

(51) Int. Cl.
*A61M 25/16*    (2006.01)
*A61M 25/00*    (2006.01)
(Continued)

(52) U.S. Cl.
CPC .... *A61M 25/0054* (2013.01); *A61M 25/0009* (2013.01); *B32B 37/06* (2013.01);
(Continued)

(58) Field of Classification Search
CPC .......... A61M 25/0009; A61M 25/0012; A61M 25/0043; A61M 25/0045; A61M 25/0053;
(Continued)

(56) References Cited

U.S. PATENT DOCUMENTS 4,251,305 A    2/1981    Becker et al.
4,775,371 A    10/1988   Mueller, Jr.
(Continued)

FOREIGN PATENT DOCUMENTS

EP    1435252 A1    7/2004

OTHER PUBLICATIONS

Pebax Processing, Polyether Block Amides (Pebax): Injection Molding Brochure, Arkema Inc., pp. 1-7.
(Continued)

*Primary Examiner* — Katherine Rodjom
(74) *Attorney, Agent, or Firm* — Seager, Tufte & Wickhem, LLP (57) ABSTRACT

A multi-section tubular member including a sleeve surrounding and bridging a joint between a first section and a second section of the tubular member, and a method of forming a multi-section tubular member are disclosed. A polymeric sleeve may extend over a portion of the first section and an adjoining portion of the second section. A length of heat shrink tubing may be placed over the sleeve and heated, thereby compressing the heat shrink tubing around the sleeve. The sleeve may then be thermally bonded to each of the first section and the second section. The heat shrink tubing may then be removed, leaving the sleeve securely joining the first section and the second section to form a multi-section tubular member.

16 Claims, 9 Drawing Sheets

Related U.S. Application Data continuation of application No. 11/279,985, filed on Apr. 17, 2006, now Pat. No. 7,678,223.

(51) Int. Cl.
  *B32B 37/06* (2006.01)
  *B32B 37/10* (2006.01)
  *B32B 37/18* (2006.01)
  *B32B 38/10* (2006.01)
  *B32B 38/00* (2006.01)

(52) U.S. Cl.
  CPC ............ *B32B 37/10* (2013.01); *B32B 37/182* (2013.01); *B32B 38/10* (2013.01); *A61M 25/0052* (2013.01); *B32B 2038/0052* (2013.01); *B32B 2307/30* (2013.01); *B32B 2535/00* (2013.01); *B32B 2597/00* (2013.01)

(58) Field of Classification Search
  CPC ............... A61M 25/0054; B32B 37/06; B32B 2535/00; B32B 2597/00
  See application file for complete search history.

(56) References Cited

U.S. PATENT DOCUMENTS

| | | |
|---|---|---|
| 5,156,594 A | 10/1992 | Keith |
| 5,160,559 A | 11/1992 | Scovil et al. |
| 5,195,969 A | 3/1993 | Wang et al. |
| 5,267,959 A | 12/1993 | Forman |
| 5,304,134 A | 4/1994 | Kraus et al. |
| 5,366,442 A | 11/1994 | Wang et al. |
| 5,501,759 A | 3/1996 | Forman |
| 5,569,221 A | 10/1996 | Houser et al. |
| 5,797,877 A | 8/1998 | Hamilton et al. |
| 5,843,032 A | 12/1998 | Kastenhofer |
| 5,961,765 A | 10/1999 | Kastenhofer |
| 6,027,477 A | 2/2000 | Kastenhofer |
| 6,059,769 A | 5/2000 | Lunn et al. |
| 6,063,318 A | 5/2000 | Houser et al. |
| 6,139,525 A | 10/2000 | Davis-Lemessy et al. |
| 6,165,166 A | 12/2000 | Samuelson et al. |
| 6,245,053 B1 | 6/2001 | Benjamin |
| 6,409,863 B1 | 6/2002 | Williams et al. |
| 6,464,683 B1 | 10/2002 | Samuelson et al. |
| 6,471,673 B1 | 10/2002 | Kastenhofer |
| 6,500,285 B2 | 12/2002 | Pepin et al. |
| 6,503,353 B1 | 1/2003 | Peterson et al. |
| 6,589,226 B1 | 7/2003 | Owens |
| 6,595,217 B1 | 7/2003 | Case et al. |
| 6,659,977 B2 | 12/2003 | Kastenhofer |
| 6,699,273 B2 | 3/2004 | Langan |
| 6,740,191 B2 | 5/2004 | Clarke et al. |
| 6,860,960 B1 | 3/2005 | Flanagan |
| 6,923,787 B2 | 8/2005 | Wang |
| 6,939,321 B2 | 9/2005 | Wang |
| 2001/0016702 A1 | 8/2001 | Benjamin |
| 2002/0082637 A1 | 6/2002 | Lumauig |
| 2003/0009114 A1 | 1/2003 | Chin et al. |
| 2003/0088265 A1 | 5/2003 | Kastenhofer |
| 2003/0135231 A1 | 7/2003 | Goodin et al. |
| 2003/0141002 A1 | 7/2003 | Flanagan |
| 2003/0149465 A1 | 8/2003 | Heidner et al. |
| 2003/0199852 A1* | 10/2003 | Seward ............... A61M 25/001 604/533 |
| 2003/0211258 A1 | 11/2003 | Sridharan et al. |
| 2004/0210211 A1 | 10/2004 | Devens, Jr. et al. |
| 2004/0236310 A1 | 11/2004 | Chin et al. |
| 2004/0256049 A1 | 12/2004 | O'Shaughnessy et al. |
| 2005/0131445 A1 | 6/2005 | Holman et al. |
| 2005/0211679 A1 | 9/2005 | Chiu et al. |
| 2006/0074401 A1 | 4/2006 | Ross |

OTHER PUBLICATIONS

All non-patent literature documents and foreign patent documents have been previously uploaded in parent U.S. Appl. No. 12/724,264, filed Mar. 15, 2010.

* cited by examiner

CATHETER HAVING A MULTI-SECTION TUBULAR MEMBER AND METHOD OF MAKING THE SAME

RELATED APPLICATIONS

This application is a continuation of U.S. application Ser. No. 12/724,264 filed Mar. 15, 2010, which is a continuation of U.S. application Ser. No. 11/279,985 filed Apr. 17, 2006, now U.S. Pat. No. 7,678,223.

TECHNICAL FIELD

The invention generally relates to medical devices. More specifically, the invention relates to a medical device, such as a catheter, including a multi-section tubular member, and methods of joining multiple sections of a tubular member.

BACKGROUND

Elongated medical devices are commonly used to facilitate navigation through and/or treatment within the anatomy of a patient. A variety of elongate medical devices for intracorporeal use, such as catheters, endoscopes, guidewires and the like, have been developed over the past several decades. Because the anatomy of a patient may be very tortuous, it is often desirable to combine a number of performance features in such devices. For example, it is sometimes desirable that the device have a relatively high level of pushability and torqueability, particularly near its proximal end. It is also sometimes desirable that a device be relatively flexible, particularly near its distal end.

A number of different elongated medical device structures and assemblies are known, each having certain advantages and disadvantages. However, there is an ongoing need to provide alternative elongated medical device structures, assemblies, and methods.

One such elongate medical device, a balloon catheter, can include an inflatable and deflatable balloon carried by a long narrow catheter body. The balloon is initially folded around the catheter body to reduce the radial profile of the balloon catheter for easy insertion into the body. During use, the balloon may be inflated and later deflated at a selected location within the body.

One common balloon catheter design includes a coaxial arrangement of an inner tubular member surrounded by an outer tubular member. The inner tubular member typically includes a lumen that can be used for delivery of the device over a guidewire. The annular space between the inner tubular member and the outer tubular member typically defines an inflation lumen in fluid communication with the balloon, wherein an inflation fluid passes through during inflation and deflation of the balloon. It is important that the inflation lumen remain substantially open and unobstructed during inflation and deflation of the balloon to insure proper inflation and deflation of the balloon.

Some such catheters may utilize tubular members having multiple sections of dissimilar materials joined together by thermally bonding the sections together to provide regions of varying flexibility. There is an ongoing need to provide new structures and methods of joining multiple sections of a catheter shaft without compromising the desired characteristics of the catheter shaft.

SUMMARY

The invention is directed to elongate medical devices, such as catheters, having one or more multi-section tubular members and methods of forming the same. The one or more sections may be joined together with a polymeric tubular sleeve, while maintaining the low profile of the tubular member or other advantageous attributes of the tubular member.

Accordingly, one embodiment of the invention is a balloon catheter having an outer tubular member, an inner tubular member, and an inflatable balloon. The inner tubular member may include a first, proximal section and a second, distal section. The proximal section may abut the distal section, and a polymeric sleeve may be used to secure the proximal section to the distal section, thus forming a joint between the proximal section and the distal section.

Another aspect of the invention is a method of forming a multi-section tubular member for use in an elongate medical device. A first tubular section and a second tubular section of a tubular member are placed longitudinally end-to-end, such that an end of the first tubular member abuts the end of the second tubular member, wherein the region of abutment defines a junction between the first and second tubular members. A polymeric tubular sleeve is then placed over the first and second sections such that the sleeve extends proximally and distally from the junction between the first and second tubular members. A length of tubing, such as heat shrink tubing, is placed over and surrounds the polymeric sleeve. Thermal energy is applied to the heat shrink tubing to compress the heat shrink tubing around the sleeve and tubular members. Thermal energy is applied to the polymeric sleeve, elevating the temperature of the sleeve and the adjacent surface of the corresponding portion of the tubular members, thereby creating a bond between the polymeric sleeve and each of the first tubular member and the second tubular member. The heat shrink tubing is then removed from the tubular members and sleeve.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

BRIEF DESCRIPTION OF THE DRAWINGS

The invention may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Although some suitable dimensions of various embodiments are disclosed herein, one of skill in the art would understand that desired dimensions may deviate from those expressly disclosed, unless clearly stated to the contrary.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 1:
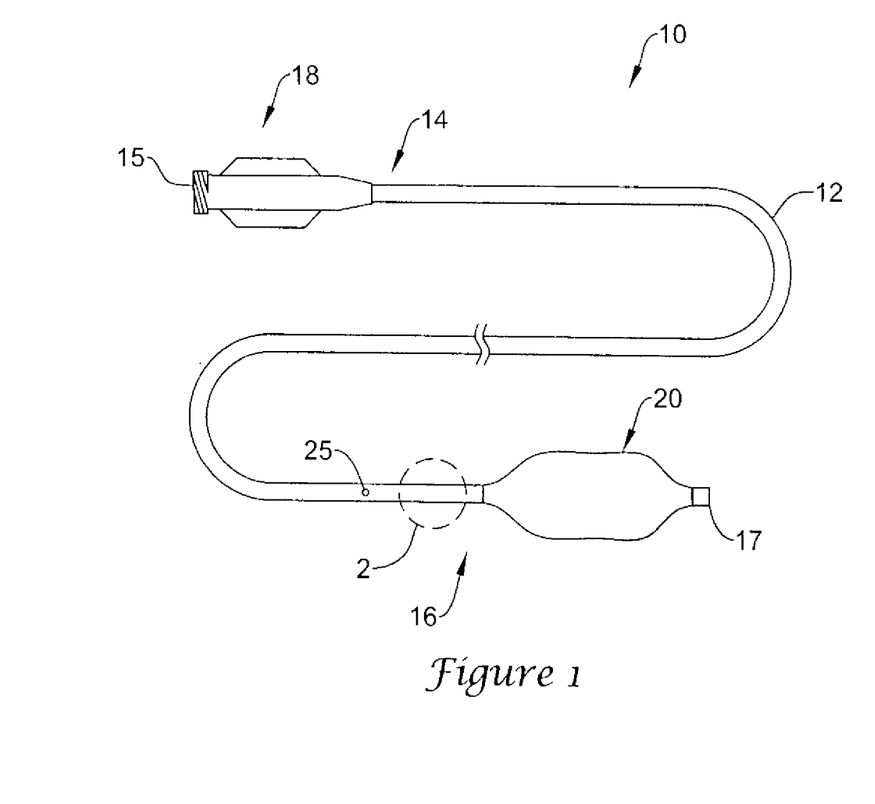
FIG. 1 is a plan view of an illustrative balloon catheter in accordance with the invention.

Refer now to FIG. 1, which illustrates a catheter 10 in accordance with one example embodiment. The catheter 10 may be one of a variety of different catheters, but is preferably an intravascular catheter. Examples of some exemplary intravascular catheters include microcatheters, drug delivery catheters, diagnostic catheters, guide catheters, balloon catheters, stent delivery catheters, embolic coil delivery catheters, and atherectomy catheters. FIG. 1 illustrates a balloon catheter having a proximal end 15 and a distal end 17. In general, the catheter 10 may include a generally elongate shaft 12. A hub assembly 18 may be coupled to the proximal portion 14 of the elongate shaft 12 and an inflatable balloon 20 may be coupled to the distal portion 16 of the elongate shaft 12.

The elongate shaft 12 may have a length and an outside diameter appropriate for its desired use, for example, to enable intravascular insertion and navigation. For example, in some embodiments, the elongate shaft 12 may have a length in the range of about 1 to about 300 cm or more, or in some embodiments in the range of about 20 to about 250 cm, and an outside diameter in the range of about 1F (French) to about 20F, or in some embodiments, in the range of about 1F to about 10F.

The catheter 10 may be an over-the-wire (OTW) type catheter or the catheter 10 may be a single-operator-exchange (SOE) type catheter, for instance. Typically, an OTW catheter is configured such that a guidewire may extend within a lumen of the elongate shaft 12 substantially the entire length of the catheter 10. On the other hand, a SOE catheter is typically configured with a distal guidewire port 25 proximal of the balloon 20, but distal of the proximal end 15 of the catheter 10. (It is noted that the guidewire port 25 shown in FIG. 1 is typically not present in an OTW type catheter). The guidewire port 25 provides an opening in the elongate shaft 12, such that a guidewire (not shown) may extend within a lumen of the elongate shaft 12 through a distal region of the catheter 10, but may be located exterior of the elongate shaft 12 throughout a proximal portion of the catheter 10.

Figure 2:
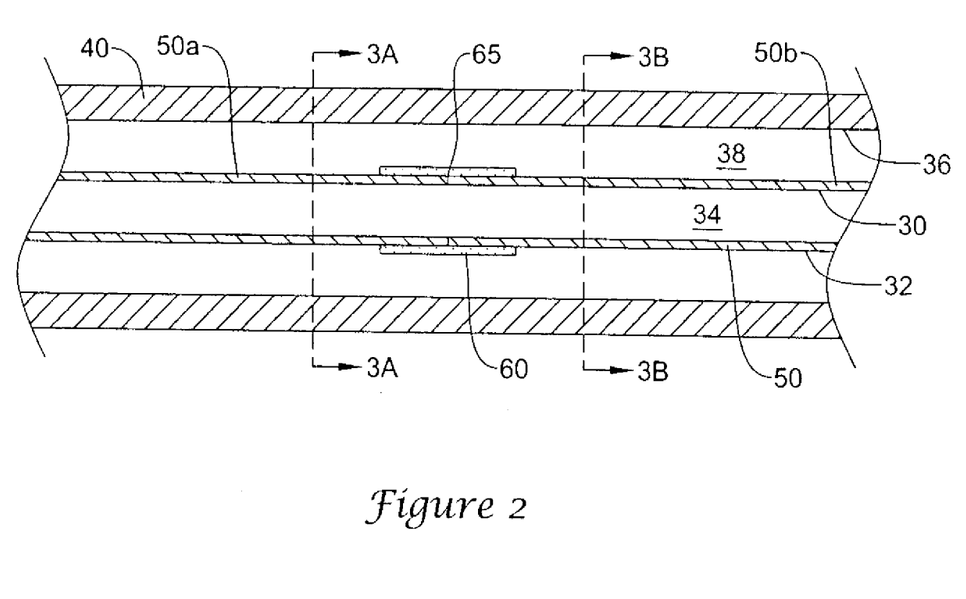
FIG. 2 is a cross-sectional view of a portion of the illustrative balloon catheter of FIG. 1.

FIG. 2 shows a partial cross-sectional view of a portion of the elongate shaft 12. The portion of the elongate shaft 12 shown in FIG. 2 may be a portion of the elongate shaft 12 located proximal of the balloon 20. However, in other embodiments, the portion of the elongate shaft 12, as shown in FIG. 2, may be located at a different position along the catheter 10. For instance, the portion shown in FIG. 2 may be located beneath the proximal waist of the balloon 20 or may be located beneath a midsection of the balloon 20. The elongate shaft 12 may include an outer tubular member 40 and an inner tubular member 50 extending through at least a portion of the outer tubular member 40. In the case of an over-the-wire type (OTW) catheter, the inner tubular member 50 may extend through substantially the entire length of the outer tubular member 40, from the proximal portion of the elongate shaft 12 to the distal portion of the elongate shaft 12. Thus, a guidewire may be inserted through the inner tubular member 50 and extend substantially the entire length of the elongate shaft 12. In the case of a single-operator-exchange type (SOE) catheter, the inner tubular member 50 may extend through a distal portion of the outer tubular member 40, from the guidewire port 25 to the distal end of the catheter. Thus, a guidewire may be inserted through the guidewire port 25 into the inner tubular member 50 and extend to the distal end of the elongate shaft 12. In a SOE catheter, the inner tubular member 50 may not be present in the proximal portion of the elongate shaft 12.

In some embodiments, the distal end of the outer tubular member 40 may be secured to the proximal waist of the balloon 20 and the inner tubular member 50 may be coaxially disposed in the outer tubular member 40 and may extend distal of the distal end of the outer tubular member 40 through the balloon 20 such that the distal end of the inner tubular member 50 is secured to the distal waist of the balloon 20. The balloon 20 may be secured to the tubular members 40, 50 by laser bonding, RF bonding, adhesive, or other means known in the art.

The inner tubular member 50 may have an inner surface 30 and an outer surface 32. The inner surface 30 may define a lumen 34, for example a guidewire lumen. The inner tubular member 50 may be coaxial with the outer tubular member 40, such that the space between the outer surface 32 of the inner tubular member 50 and the inner surface 36 of the outer tubular member 40 defines a lumen 38, for example an annular inflation lumen. The inflation lumen 38 may be in fluid communication with the balloon 20 and the hub assembly 18.

The inner tubular member 50 may include a first, proximal section 50A and a second, distal section 50B. When describing the first section 50A as a proximal section and the second section 50B as a distal section, the intention is to describe the first section 50A as being located proximal of the second section 50B. It is not the intention to imply the proximal section 50A is necessarily located in the proximal portion 14 of the catheter 10, although in some embodiments that may be the case. The proximal section 50A may be a single layer or a multi-layered tubular member. The proximal section 50A may include 1, 2, 3, 4, 5, 6 or more layers. The distal section 50B may be a single layer or a multi-layered tubular member. The distal section 50B may include 1, 2, 3, 4, 5, 6 or more layers. Additionally, the intention is not to limit the inner tubular member 50 as having only two distinct sections, but in some embodiments, the inner tubular member 50 may include additional sections as desired, which may or may not be similarly joined together as described herein. For example, the inner tubular member 50 may include three, four, five or more distinct tubular sections joined together.

The proximal end of the distal section 50B and the distal end of the proximal section 50A may be positioned end-to-end, in an abutting orientation, or in another joining orientation. The interface between the proximal section 50A and the distal section 50B defines a joint 65. Although the joint 65 shown in FIG. 2 is a butt joint, the joint may alternatively be an overlapping joint, tapering joint, or the like. A polymeric tubular sleeve 60 may be disposed over the joint 65 and may extend proximally of the joint 65 for a length and distally of the joint 65 for a length. Thus, the sleeve 60 may bridge the joint 65. The sleeve 60, in the embodiment shown, desirably has a low profile, thus not appreciably obstructing the annular inflation lumen 38.

Although the joint 65 is shown in FIGS. 1 and 2 to be located proximal of the balloon 20, in some embodiments, the joint 65 joining two sections of the inner tubular member 50 may be located at a location underlying the proximal waist of the balloon 20 or the joint 65 may be located at a location underlying the body of the balloon 20. Alternatively, the location of the joint 65 may be located at another position along the catheter 10.

The sleeve 60 may be desirably formed of a thin, thermoplastic material. Some example materials may include, but are not limited to, polyamide, polyether block amide, polyurethane, silicone rubber, nylon, polyethylene, fluorinated hydrocarbon polymers, and the like. For example, in some particular examples the sleeve 60 is 100% polyamide 6, polyamide 12, or thermoplastic polyurethane. Some polymer materials suitable for use in the sleeve 60 are sold under the trademarks of PEBAX, PELLETHANE, TEXIN and VESTAMID.

The sleeve 60 may be formed by extrusion, drawing, injection molding, blow molding, or the like. In some embodiments, the sleeve 60 may be formed of a polymeric material having highly oriented molecular chains. In some embodiments, the molecular chains of the sleeve 60 may be highly oriented in a longitudinal direction. In other words, the molecular chains may be longitudinally aligned with one another along the longitudinal axis of the sleeve 60. Thus, the molecular chains may be arranged and stretched in a longitudinal orientation. Such an orientation may provide the sleeve 60 with increased tensile strength. In some embodiments, the molecular chains of the sleeve 60 may be highly oriented in a circumferential direction. In other words, the molecular chains may be circumferentially aligned with one another around the circumference of the sleeve 60. Thus, the molecular chains may be arranged and stretched in a circumferential orientation. Such an orientation may provide the sleeve 60 with increased hoop strength. In some embodiments, the molecular chains of the sleeve 60 may be highly oriented in a helical direction. In other words, the molecular chains may be helically aligned with one another to form a helix along the length of the sleeve 60. Thus, the molecular chains may be arranged and stretched in a helical orientation. Such an orientation may provide the sleeve 60 with increased torsional strength.

Figure 3A:
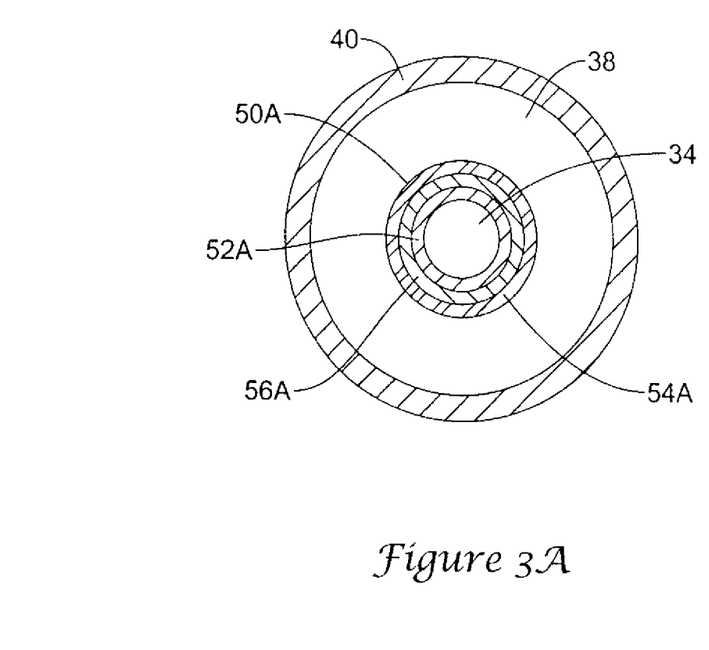
FIG. 3A is a cross-sectional view taken along line 3A-3A of FIG. 2.

FIG. 3A shows a cross-sectional view of the catheter shaft 12 taken along line 3A-3A of FIG. 2. The proximal section 50A of the inner tubular member 50 shown in FIG. 3A is a multi-layer section shown as a tri-layer section having three layers; an inner layer 52A, an outer layer 54A, and an intermediate or tie layer 56A interposed between the inner layer 52A and the outer layer 54A. However, in other embodiments, the proximal section 50A of the inner tubular member 50 may be a single layer tubular member, a bi-layer tubular member, or other multi-layered tubular member.

Figure 3B:
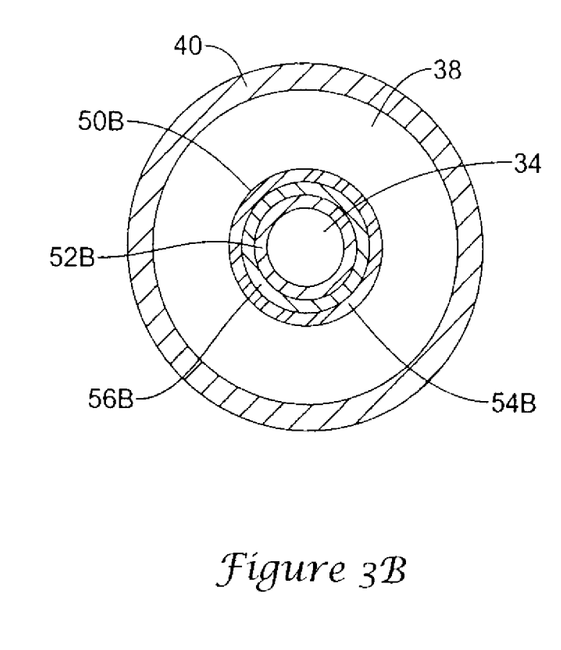
FIG. 3B is a cross-sectional view taken along line 3B-3B of FIG. 2.

FIG. 3B shows a cross-sectional view of the catheter shaft 12 taken along line 3B-3B of FIG. 2. The distal section 50B of the inner tubular member 50 shown in FIG. 3B is a multi-layer section shown as a tri-layer section having three layers; an inner layer 52B, an outer layer 54B, and an intermediate or tie layer 56B interposed between the inner layer 52B and the outer layer 54B. However, in other embodiments, the distal section 50B of the inner tubular member 50 may be a single layer tubular member, a bi-layer tubular member, or other multi-layered tubular member.

In both, the proximal and distal sections 50A, 50B, the inner layer 52A, 52B may include a lubricious polymer having a low coefficient of friction to facilitate advancement of a guidewire therethrough. In some embodiments, the inner layer 52A, 52B may be formed of high radial strength, hard, low-friction polymer that resists collapse during balloon inflation and facilitates movement of the catheter over a guidewire. Some suitable polymers include high density polyethylene (HDPE), or a fluorocarbon-based polymer, such as polytetrafluoroethylene (PTFE) or a copolymer of tetrafluoroethylene with perfluoroalkyl vinyl ether (PFA) (more specifically, perfluoropropyl vinyl ether or perfluoromethyl vinyl ether), or the like, or graphite-filled nylons. One particular example of a high density polyethylene is Marlex 4903, available from Chevron Phillips.

The intermediate layers 56A, 56B of the proximal and distal sections 50A, 50B of the inner tubular member 50 may be a tie layer that facilitates bonding between the inner layer 52A, 52B and the outer layer 52A, 52B of each of the proximal and distal sections 50A, 50B. Some suitable polymers for the intermediate layer 56A, 56B include maleic anhydride functionalized linear low-density polyethylene. One example of which is Plexar PX-380, available from Equistar, Houston, Tex.

The material for the outer layers 54A, 54B of the inner tubular member 50 may be selected for their individual mechanical characteristics, such as pushability and/or trackability. The material chosen for the outer layer 54A of the proximal section 50A may be a stiffer material than the material chosen for the outer layer 54B of the distal section 50B. However, in some embodiments, it may be desirable that the material chosen for the outer layer 54A of the proximal section 50A is more flexible than the material chosen for the outer layer 54B of the distal section 50B. The flexibility or stiffness of a polymer may be characterized by its flexural modulus, which is the ratio of stress to strain in flexural deformation. In some embodiments, the flexural modulus of the outer layer 54B of the distal section 50B is about 75% less than or more than 75% less than the flexural modulus of the outer layer 54A of the proximal section 50A. In some embodiments, the flexural modulus of the distal outer layer 54B is about 15 to about 500 MPa and the flexural modulus of the proximal outer layer 54A is about 700 to about 4000 MPa.

Some examples of suitable polymers may include, but are not limited to, elastomers, such as thermoplastic elastomers, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester and their copolymers, blends, mixtures or combinations thereof. Some examples include polyamides such as polyamide 12, and blends thereof.

For instance, in some embodiments, the proximal outer layer 54A may be a blend of about 40% to about 70%, or about 45% to about 60%, by weight of an amorphous polyamide, such as amorphous polyamide 12, and about 30% to about 55%, or about 40% to about 55%, by weight of a non-amorphous polyamide, such as non-amorphous polyamide 12. In a particular example, the proximal outer layer 54A is a blend of 45% amorphous polyamide 12 and 55% non-amorphous polyamide 12. The flexural modulus of the blend may be about 1000 to about 2000 MPa, or about 1400 to about 1600 MPa. In another example, the proximal outer layer 54A is a blend of 60% amorphous polyamide 12 and 40% non-amorphous polyamide 12. The flexural modulus of the blend may be about 1000 to about 2000 MPa, or about 1400 to about 1600 MPa.

In some embodiments, the distal outer layer 54B may be a blend of polyether block amide resins. For instance, the distal outer layer 54B may be a blend of about 40% to about 80% by weight of a polyether block amide having a Shore durometer hardness of about 60D to about 80D, and about 20% to about 60% by weight of a polyether block amide having a Shore durometer hardness of about 50D to about 65D. In some embodiments, the flexural modulus of the blend may be about 300 to about 500 MPa. In a particular example, the distal outer layer 54B is a blend of 75% of a polyether block amide having a Shore durometer hardness of about 70D and 25% of a polyether block amide having a Shore durometer hardness of about 55D. The flexural modulus of the blend may be about 400 MPa. In another example, the distal outer layer 54B is a blend of 40% of a polyether block amide having a Shore durometer hardness of about 70D and 60% of a polyether block amide having a Shore durometer hardness of about 63D. The flexural modulus of the blend may be about 390 MPa. The proximal section 50A and the distal section 50B may be separately manufactured, such as by co-extrusion, and then joined together with a polymeric sleeve as described herein.

A method of joining the proximal section 50A and the distal section 50B of the inner tubular member 50 in a longitudinal, end-to-end orientation utilizing a sleeve overlying a portion of each of the proximal section 50A and the distal section 50B will now be described in conjunction with FIGS. 4-8. However, it is noted that other joining orientations of the proximal section 50A and the distal section 50B of the inner tubular member 50 may benefit from the disclosed joining method.

Figure 4:
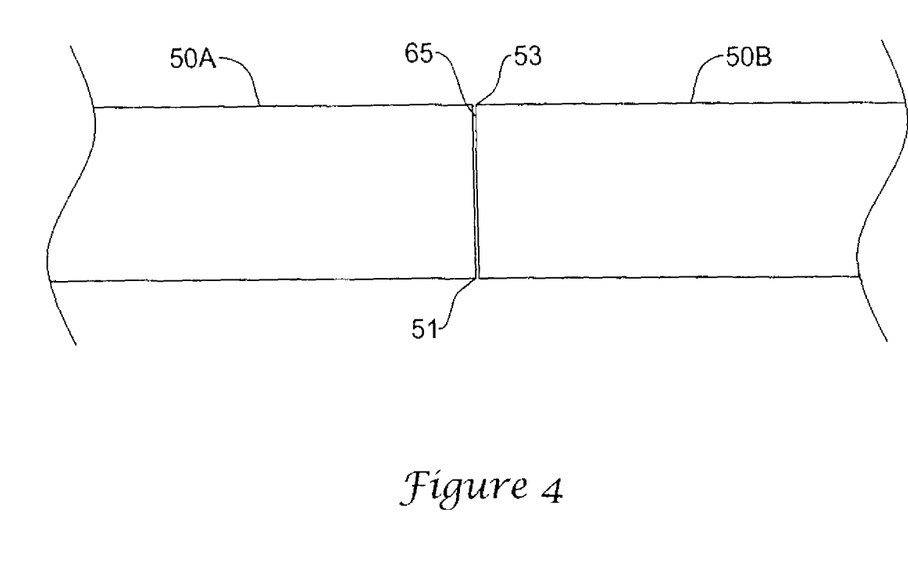
FIGS. 4-8 illustrate a method of joining two tubular segments in accordance with the invention.

As shown in FIG. 4, the proximal section 50A and the distal section 50B may be placed end-to-end in an abutting relationship, such that the distal end 51 of the proximal section 50A abuts the proximal end 53 of the distal section 50B at joint 65. The joint 65 may be a butt joint as shown throughout the present description, however, in some embodiments the joint may alternatively be an overlapping joint, a tapering joint, or the like. The distal end 51 of the proximal section 50A may be in contact with the proximal end 53 of the distal section 50B, or, in some embodiments, a small space or gap may remain between the ends 51, 53. In some embodiments, a mandrel, such as a polytetrafluoroethylene (e.g., Teflon) coated mandrel, may be inserted through the lumen 34 of the proximal section 50A and the distal section 50B. The sections 50A, 50B may be slid over the mandrel, which may provide interior support to maintain the structure of the tubular member 50 and preserve the patency of the tubular lumen 34 throughout the manufacturing process.

The tubular sections 50A, 50B may be appropriately sized as known in the art. For example, in some embodiments the proximal section 50A may have an outer diameter of about 0.01 to about 0.05 inches, or about 0.02 to about 0.04 inches, or about 0.02 inches. In some embodiments, the proximal section 50A may have an appropriate inner diameter creating a wall thickness of about 0.002 to about 0.005 inches. In some embodiments, the distal section 50B may have dimensions similar to those of the proximal section 50A. In some embodiments, the distal section 50B may have a distal portion having a reduced diameter, wherein the proximal portion may have dimensions similar to those of the proximal section 50A and the distal portion may have an outer diameter of about 0.01 to about 0.04 inches, or about 0.01 to about 0.03 inches, or about 0.01 to about 0.02 inches, and/or an inner diameter creating a wall thickness of about 0.002 to about 0.005 inches. The distal section 50B may have a tapered portion between the proximal portion and the distal portion forming a transition between the proximal portion and the reduced diameter distal portion.

Figure 5:
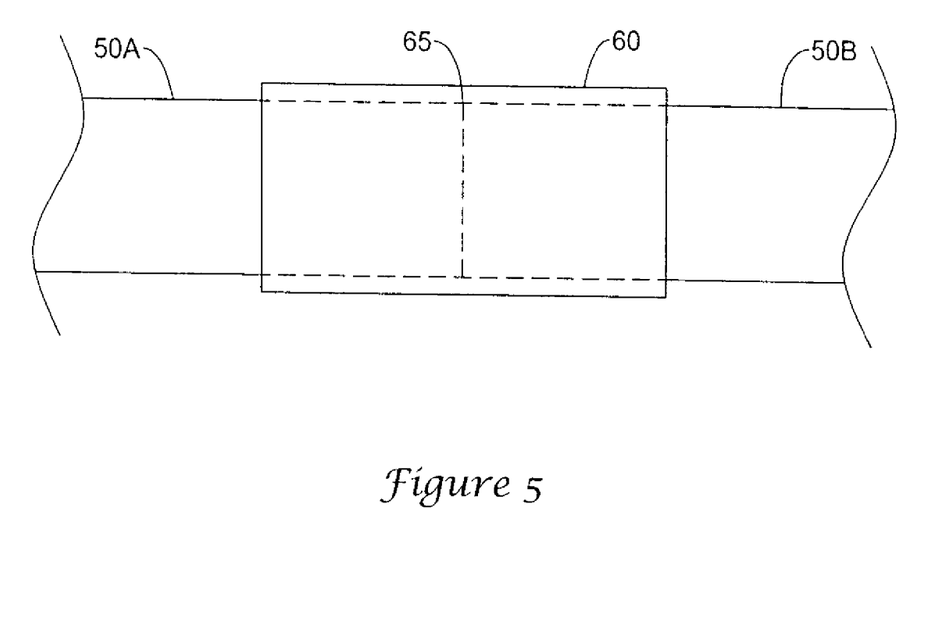

Referring to FIG. 5, a sleeve 60, such as a polymeric tubular sleeve, may be placed over the joint 65 between the proximal section 50A and the distal section 50B. The sleeve 60, which in some embodiments may be preformed such as by extrusion or drawing, may be slid over the tubular sections 50A, 50B, such that a portion of the sleeve 60 is located proximal of the joint 65 and a portion of the sleeve 60 is located distal of the joint 65. In other words, the sleeve 60 may be positioned so as to bridge the joint 65 between the tubular sections 50A, 50B, overlying a portion of each of the tubular sections 50A, 50B. In some embodiments, the sleeve 60 may be approximately centered over the joint 65. The sleeve 60 may be any desired length. For example, in some embodiments the sleeve 60 may be about 2 to about 20 mm in length, about 3 to about 10 mm in length, about 4 to about 6 mm in length, or about 5 mm in length.

The sleeve 60 may be appropriately sized. For example, the inner diameter of the sleeve 60 may be chosen to closely approximate the outer diameter of the tubular sections 50A, 50B adjacent joint 65. In some embodiments, the sleeve 60 may have a wall thickness of about 0.0002 to about 0.005 inches, or about 0.0005 to about 0.002 inches, or about 0.0002 to about 0.001 inches, or about 0.0005 inches. In some embodiments, the sleeve 60 may be dimensioned so as not to measurably increase the outer diameter of the inner tubular member 50 near the joint 65. Therefore, when bonded to the tubular sections 50A, 50B, the sleeve 60 may not appreciably obstruct the inflation lumen 38.

Figure 6:
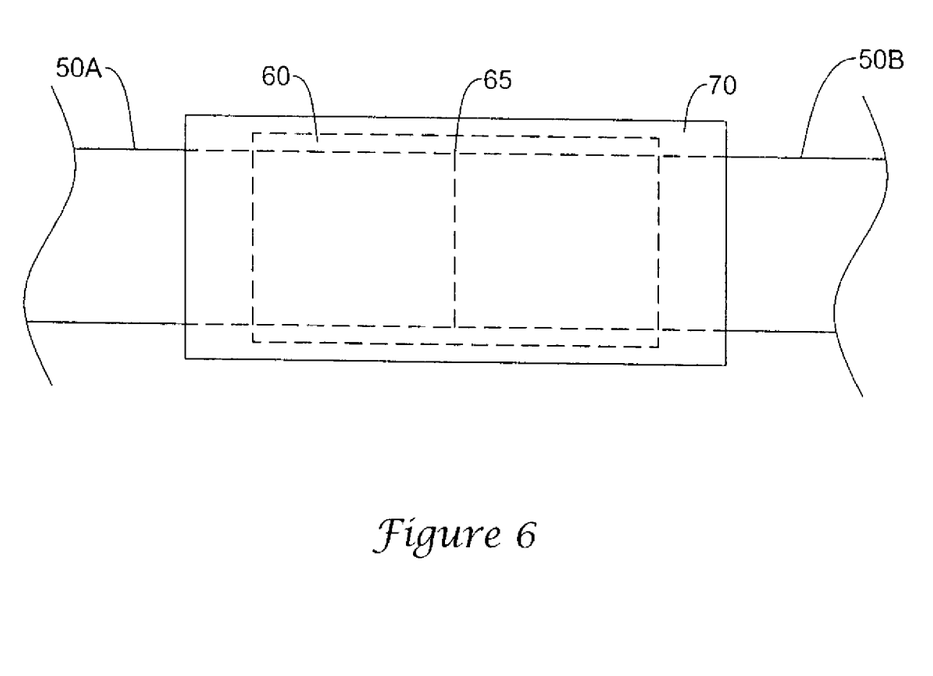

As illustrated in FIG. 6, a length of tubing, such as a length of heat shrink tubing 70, may then be positioned over the sleeve 60 and a portion of each of the tubular sections 50A, 50B, such that the heat shrink tubing 70 extends beyond the extents of the sleeve 60. In some embodiments, the heat shrink tubing 70 may have a length of about 10 to about 50 mm, or about 20 to about 40 mm, or about 30 mm.

The heat shrink tubing 70 may be chosen to have a higher melting temperature than each of the sleeve 60, the outer layer 54A of the proximal section 50A, and the outer layer 54B of the distal section 50B. For example, the sleeve 60 may be a polymeric material of about 100% polyamide 12 having a melting temperature of about 350° F., the proximal outer layer 54A may be a polymeric blend of amorphous polyamide 12 and non-amorphous polyamide 12 have a melting temperature of about 350° F. to about 375° F., and the distal outer layer 54B may be a polymeric blend of polyether block amide resins have a melting temperature of about 340° F. to about 350° F. Thus, in some embodiments, the heat shrink tubing 70 may have a melting temperature greater than 375° F. In some embodiments, the heat shrink tubing 70 may have a melting temperature appreciably greater than 375° F. For example, the heat shrink tubing 70 may have a melting temperature generally greater than the greatest melting temperature of the sleeve 60, the outer layer 54A of the proximal section 50A, and the outer layer 54A of the distal section 50B. For example, in some embodiments, the melting temperature of the heat shrink tubing 70 may be at least 1.2 times or more, 1.5 times or more, 2 times or more, 2.5 times or more, or 3 times or more of the greatest melting temperature of the sleeve 60, the outer layer 54A of the proximal section 50A, and the outer layer 54A of the distal section 50B. Generally, the heat shrink tubing 70 may have a melting temperature that would not impair or destroy the integrity of the joined region of the catheter 10.

Figure 7:
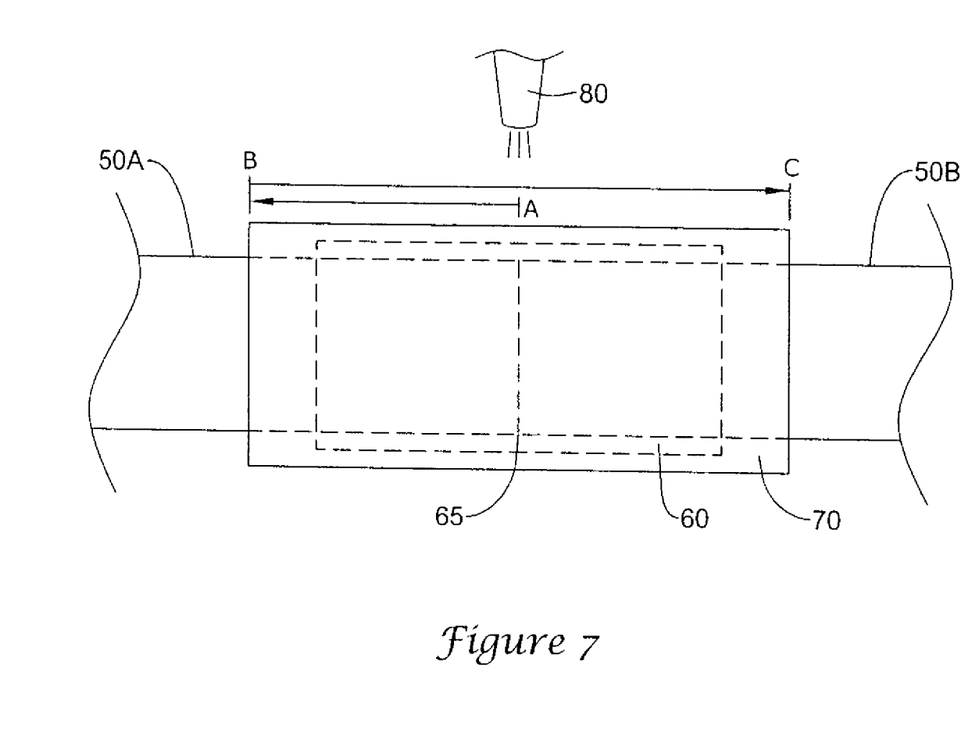

Referring to FIG. 7, thermal energy may be applied to the heat shrink tubing 70 such that the heat shrink tubing 70 is contracted around the sleeve 60 and a portion of each of the proximal section 50A and the distal section 50B. Contraction of the heat shrink tubing 70 may provide a compressive force directed radially inward on the sleeve 60 and/or the proximal section 50A and the distal section 50B. The compressive force exerted by the heat shrink tubing 70 may secure the sleeve 60 and the sections 50A, 50B of the tubular member 50 in a desired orientation, and assist in bonding the sleeve 60 to each of the proximal section 50A and the distal section 50B of the tubular member 50. The heat shrink tubing 70 may provide sufficient force to fix the proximal section 50A and the distal section 50B, forming a smooth transition between the proximal section 50A and the distal section 50B without generating excess flow of material from the bond site. The heat shrink tubing 70 may be selected to generate a high level of compressive force through contraction of the heat shrink tubing 70 when subjected to heat. In some embodiments, the heat shrink tubing 70 may be selected to exert a compressive force of about 20 grams or greater, about 25 grams or greater, or about 30 grams or greater on the underlying sleeve 60. In some embodiments, the compressive force may be about 25 to about 32 grams.

Concurrently, or in a subsequent step, thermal energy may be applied to the sleeve 60, the proximal section 50A of the tubular member 50 and/or the distal section 50B of the tubular member 50. The thermal energy may elevate the temperature of the sleeve 60, the proximal section 50A, and/or the distal section 50B in order to induce bonding of the sleeve 60 to each of the proximal section 50A and the distal section 50B. For example, the applied thermal energy may elevate the temperature of the sleeve 60, the portion of the outer layer 54A of the proximal section 50A underlying the sleeve 60, and/or the portion of the outer layer 54B of the distal section 50B underlying the sleeve 60 at or above its respective melt temperature. The combination of the compressive force generated by the heat shrink tubing 70 and the thermal energy heating the materials above their respective melt temperature may bond the sleeve 60 to each of the proximal section 50A and the distal section 50B. The high level of compressive force generated by the heat shrink tubing 70 may facilitate enhanced bonding of the materials. In some embodiments, the materials of the outer layers 54A, 54B and the sleeve 60 may be melt compatible or melt miscible. Thus, the materials of the proximal outer layer 54A, the distal outer layer 54B, and/or the sleeve 60 may blend or mix together to form a strong bond. In some embodiments, ionic bonds, covalent bonds, and/or chain entanglements may be formed between the sleeve 60 and each of the proximal section 50A and the distal section 50B.

Thermal energy may be applied by a laser welding process using a laser 80, such as a YAG laser, a $CO_2$ laser, a diode laser, etc., or any combination thereof. Typically, a $CO_2$ laser operated at 10.6 microns produces thermal energy which may be readily absorbed by many polymeric materials. Laser energy typically heats a workpiece from the outside surface to the inside. Thus, thermal energy created by a laser, such as a $CO_2$ laser, may elevate the temperature of the outer layers of material without significantly elevating the temperature of inner layers. For example, the use of a $CO_2$ laser may heat the sleeve 60 and the outer layers 54A, 54B of the inner tubular member 50 to a temperature at or above their respective melting temperatures, without heating the inner layer 52A, 52B and/or the intermediate layer 56A, 56B above its respective melting temperature. Thus, the heat affected zone created by the laser may be limited to the interface between the sleeve 60 and the outer surface of each of the outer layers 54A, 54B of sections 50A, 50B underlying the sleeve 60. Therefore, the tubular sections 50A, 50B may be joined together with the sleeve 60 without adversely affecting the dimensions or integrity of the tubular sections 50A, 50B. Additional sources of applying thermal energy which may be used include RF heating, electromagnetic induction heating, hot jaw clamping, or the like.

In some embodiments, the path of the laser 80 may be controlled in order to apply an appropriate amount of thermal energy to select portions of the assembly. Due to the different melting temperatures of the components of the assembly, different amounts of thermal energy may be applied to different portions of the assembly. For example, a larger amount of thermal energy may be applied to the proximal section 50A and the associated portion of the sleeve 60 overlying the proximal section 50A than may be applied to the distal section 50B and the associated portion of the sleeve 60 overlying the distal section 50B. This may be accomplished by varying the power of the laser 80, varying the speed of travel of the laser 80 and/or making additional passes with the laser 80 through select portions.

As shown in FIG. 7, the path of the laser 80 may begin at an intermediate location A of the heat shrink tubing 70 proximate the joint 65 between the proximal section 50A and the distal section 50B. The laser 80 may then travel in the proximal direction B toward the proximal end of the sleeve 60 and the heat shrink tubing 70. The laser 80 may then reverse directions and travel in the distal direction C toward the distal end of the sleeve 60 and the heat shrink tubing 70. The laser 80 may emit more thermal energy along the proximal path AB between the joint 65 and the proximal end of the sleeve 60 and the heat shrink tubing 70 than on the distal portion of the path AC between the joint 65 and the distal end of the sleeve 60 and the heat shrink tubing 70. This may be accomplished by increasing the power of the laser 80 and/or decreasing the speed of travel of the laser 80 through path AB, for example.

In some embodiments, the laser may be initially positioned at the intermediate location A proximate the joint 65. The laser 80 may travel in the proximal direction toward location B and the proximal end of the heat shrink tubing 70 while emitting high power. The laser 80 may then emit low power through the return path from location B to location A. The laser 80 may again emit high power as the laser moves distally from the intermediate location A proximate the joint 65 toward the distal location C and the distal end of the heat shrink tubing 70. Thus, the proximal portion of the assembly located between the joint 65 and the proximal end of the sleeve 60 may be exposed to higher levels of thermal energy than the distal portion of the assembly located between the joint 65 and the distal end of the sleeve 60.

In other embodiments, the laser 80 may follow a different selected pathway. In some embodiments, the laser 80 may begin proximate one end of the assembly and travel toward the other end of the assembly. In some embodiments, the laser 80 may emit more thermal energy on the portion of the assembly proximal of the joint 65 than on the portion of the assembly distal of the joint 65. Such changes in the amount of thermal energy applied to a specific portion of the assembly may be controlled by varying the power of the laser and/or varying the speed of the laser through specific locations, for example.

In some embodiments, the laser 80 may use closed loop control on temperature in order to precisely and accurately control the elevated temperature of components throughout the bonding process. For example, infrared (IR) feedback technology may be used to monitor the temperature of the components of the assembly. Thus, the laser 80 using IR feedback, or other closed loop control, may precisely elevate the temperature of a specific location at or above a desired predetermined temperature, such as the melting temperature of the polymeric materials of the specific location. Therefore, IR feedback technology, or other closed loop temperature control, may precisely control the energy level and/or the speed of the laser 80 in order to elevate each portion of the assembly to a desired temperature to induce sufficient bonding of the materials.

Figure 8:
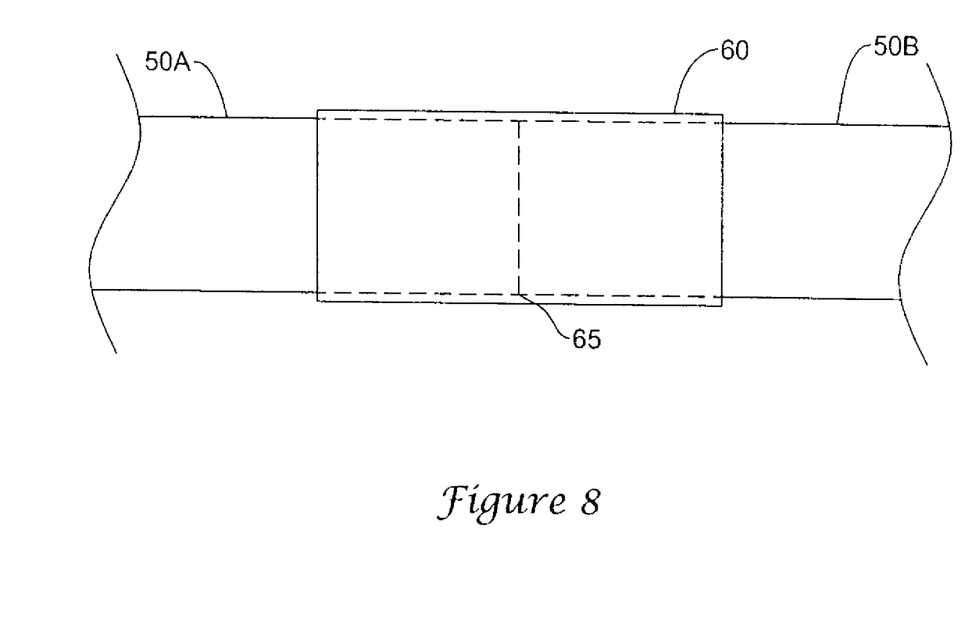

Now referring to FIG. 8, the heat shrink tubing 70 may then be removed from the tubular member 50, leaving the sleeve 60 securely bonded to both the proximal section 50A and the distal section 50B of the tubular member 50. The heat shrink tubing 70 may include a slit, notch, groove, perforations, weakened regions, or the like to facilitate removal of the heat shrink tubing from the assembly.

The sleeve 60 may bridge the joint 65 between the proximal section 50A and the distal section 50B, joining the two sections together. The compressive force of the heat shrink tubing 80 may sufficiently compress the sleeve 60 to a reduced outer diameter, thus not appreciably enlarging the outer diameter of the inner tubular member 50. Therefore, the sleeve 60 may not obstruct the inflation lumen 38 defined between the outer surface of the inner tubular member 50 and the inner surface of the outer tubular member 40 as shown in FIG. 2.

Figure 9:
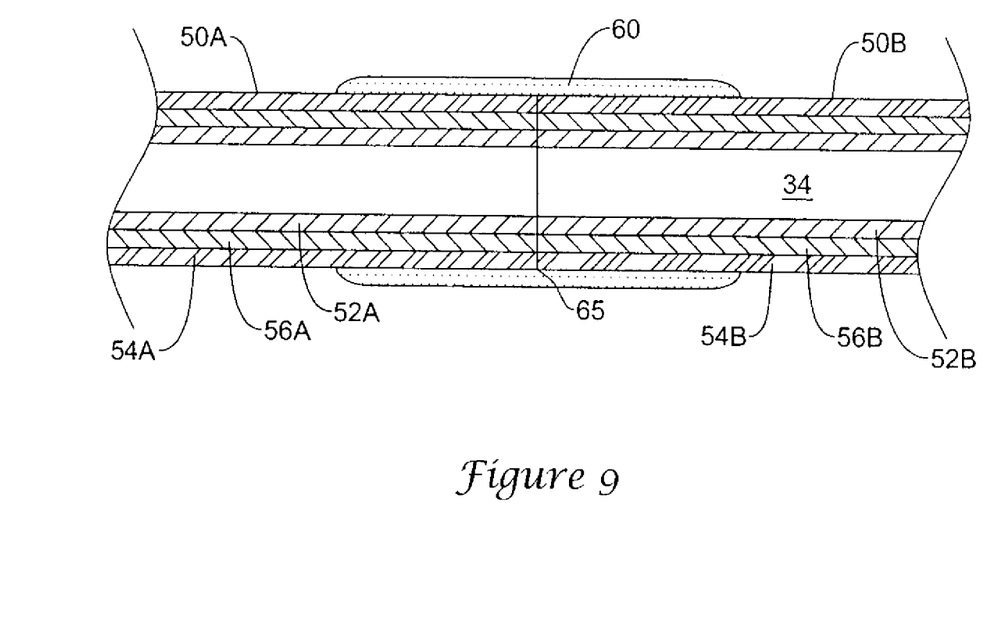
FIG. 9 is a cross-sectional view of two tubular segments joined together with a sleeve in accordance with the invention.

FIG. 9 is a cross-sectional view of the inner tubular member 50, including the sleeve 60 securely bonded to both the proximal section 50A and the distal section 50B. In some embodiments, the sleeve 60 may be securely bonded to both the proximal section 50A and the distal section 50B, while the ends 51, 53 of the proximal section 50A and the distal section 50B may remain unbonded to one another. This may be due to the focused heating emitted by the laser. The focused beam of the laser may limit the heat affected zone to only the sleeve 60 and the portion of the outer layer of the tubular members 54A, 54B underlying the sleeve 60. In some embodiments, a small gap or space may be located between the distal end 51 of the proximal section 50A and the proximal end 53 of the distal section 50B during the thermal bonding process.

Therefore, a longitudinal force typically used to bond the ends of two tubular sections together at a butt joint using RF energy is not necessary with the currently presented joining method. A longitudinal force may adversely affect the dimensions of a tubular member near the joint. As the ends of the tubular members are softened through heating, the longitudinal compressive force may deform or warp the ends of the tubular members, exceeding the tight dimensional tolerances necessary in many applications. Pooling of molten polymer material at the joint between two tubular sections may also be reduced or eliminated with the presently presented joining method.

The currently presented joining method, utilizing a polymeric sleeve and heat shrink tubing having high compressibility properties, maintains the tight dimensional tolerances necessary in many applications. Therefore, consistent results may be obtained through the currently presented method. The sleeve 60 forms a strong bond between each of the tubular sections 50A, 50B. The surface area of the bonding regions between the sleeve 60 and the tubular sections 50A, 50B is much greater than previous methods of bonding two sections with a butt joint without a sleeve.

Although the above method was herein described regarding an inner tubular member of a catheter shaft, the invention is not so restricted. It is contemplated that the method may be used in order to securely bond two sections of a multi-sectioned tubular member of any elongate medical device.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of forming a transition region of a catheter shaft, the method comprising the steps of:
providing a first tubular member having a first end and a second end;
providing a second tubular member having a first end and a second end;
abutting the first end of the first tubular member to the second end of the second tubular member such that the first and second tubular members are in an end-to-end longitudinal orientation;
placing a sleeve comprising a polymeric material having highly oriented molecular chains over a portion of the first tubular member and a portion of the second tubular member such that the sleeve extends over the first end of the first tubular member and the second end of the second tubular member;
placing a heat shrink tubing over the polymeric sleeve;
heating the heat shrink tubing, thereby compressing the heat shrink tubing around the polymeric sleeve;
thermally bonding the polymeric sleeve to the first tubular member and the second tubular member,
wherein the abutting end surfaces of the first and second tubular members are not bonded together; and
removing the heat shrink tubing.

2. The method of claim 1, wherein the step of thermally bonding the polymeric sleeve to the first tubular member and the second tubular member includes emitting thermal energy with a laser.

3. The method of claim 2, wherein the laser is a $CO_2$ laser.

4. The method of claim 1, further comprising the step of providing controlled temperature feedback to a laser during the step of thermally bonding the polymeric sleeve to the first tubular member and the second tubular member.

5. The method of claim 1, wherein the molecular chains are highly oriented in a longitudinal direction.

6. The method of claim 1, wherein the molecular chains are highly oriented in a circumferential direction.

7. The method of claim 1, wherein the molecular chains are highly oriented in a helical direction.

8. The method of claim 1, wherein the first tubular member and the second tubular member each comprises an inner layer, an outer layer, and an intermediate layer interposed between the inner layer and the outer layer.

9. The method of claim 8, wherein the outer layer of the first tubular member has a flexural modulus and the outer layer of the second tubular member has a flexural modulus different from that of the outer layer of the first tubular member.

10. The method of claim 9, wherein the flexural modulus of the outer layer of the second tubular member is about 75% less than or more than 75% less than the flexural modulus of the outer layer of the first tubular member.

11. The method of claim 1, wherein the heat shrink tubing compresses the polymeric sleeve with about 25 to about 32 grams of force.

12. A method of forming a transition region of a catheter shaft, the method comprising the steps of:

providing a first tubular member having a first end and a second end;

providing a second tubular member having a first end and a second end;

abutting the first end of the first tubular member to the second end of the second tubular member, such that the first and second tubular members are in an end-to-end longitudinal orientation;

placing a polymeric sleeve comprising a polymeric material having highly oriented molecular chains over a portion of the first tubular member and a portion of the second tubular member such that the sleeve extends over the first end of the first tubular member and the second end of the second tubular member;

placing a heat shrink tubing over the polymeric sleeve;

heating the heat shrink tubing, thereby compressing the heat shrink tubing around the polymeric sleeve, the heat shrink tubing applying a compressive force of about 20 grams or more on the sleeve;

thermally bonding the polymeric sleeve to each of the first tubular member and the second tubular member, wherein the abutting end surfaces of the first and second tubular members are not bonded together; and removing the heat shrink tubing.

13. The method of claim 12, wherein the compressive force is about 25 grams or more.

14. The method of claim 12, wherein the compressive force is about 30 grams or more.

15. The method of claim 12, wherein the molecular chains are highly oriented in a circumferential direction.

16. The method of claim 12, wherein the molecular chains are highly oriented in a helical direction.

\* \* \* \* \*